United States Patent
Steel et al.

(10) Patent No.: US 10,434,260 B2
(45) Date of Patent: Oct. 8, 2019

(54) PEN TYPE DRUG INJECTION DEVICE WITH DOSE ENCODER MECHANISM AND DOSE SETTING/DOSE DELIVERY MODE SWITCH

(71) Applicant: Sanofi-Aventis Deutschland GmbH, Frankfurt am Main (DE)

(72) Inventors: Samuel Keir Steel, Warwickshire (GB); Paul Richard Draper, Worcestershire (GB); Anthony Paul Morris, West Midlands (GB); Stephen Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 739 days.

(21) Appl. No.: 14/760,838

(22) PCT Filed: Jan. 13, 2014

(86) PCT No.: PCT/EP2014/050469
§ 371 (c)(1),
(2) Date: Jul. 14, 2015

(87) PCT Pub. No.: WO2014/111342
PCT Pub. Date: Jul. 24, 2014

(65) Prior Publication Data
US 2015/0352290 A1    Dec. 10, 2015

(30) Foreign Application Priority Data
Jan. 15, 2013  (EP) ..................... 13151373

(51) Int. Cl.
*A61M 5/315*    (2006.01)
*G01D 5/245*    (2006.01)

(52) U.S. Cl.
CPC ...... *A61M 5/3155* (2013.01); *A61M 5/31525* (2013.01); *A61M 5/31528* (2013.01);
(Continued)

(58) Field of Classification Search
CPC .......... A61M 5/31525; A61M 5/31528; A61M 5/31546; A61M 5/31548; A61M 5/3155;
(Continued)

(56) References Cited

U.S. PATENT DOCUMENTS

| | | |
|---|---|---|
| 533,575 A | 2/1895 | Wilkens |
| 5,226,895 A | 7/1993 | Harris |

(Continued)

FOREIGN PATENT DOCUMENTS

| | | |
|---|---|---|
| EP | 0937471 A2 | 8/1999 |
| EP | 0937476 A2 | 8/1999 |

(Continued)

OTHER PUBLICATIONS

International Search Report in Application No. PCT/EP2014/050469, dated May 9, 2014, 6 pages.
(Continued)

*Primary Examiner* — Shefali D Patel
(74) *Attorney, Agent, or Firm* — Fish & Richardson P.C.

(57) ABSTRACT

A drug delivery device comprising: a housing; a plurality of sensors; and a cylindrical member supported within the housing, an outer surface of said cylindrical member being provided with a helical track, the helical track comprising track segments of a first type and track segments of a second type, the first and second types of track segments being respectively capable of inducing first and second responses in the sensors; wherein: the helical track has a width; the helical track includes across the width of the helical track at least one track segment of the first type and at least one track segment of the second type at plural positions along a length
(Continued)

of the helical track; the device is configured such that during a first phase of a drug delivery operation the helical track is moved axially, without rotation, relative to the plurality of sensors between a first position and a second position, and during a second phase of the drug delivery operation the track is moved helically relative to the plurality of sensors from the second position; and responses induced in the plurality of sensors by the track segments of the helical track are different in the first position compared to responses induced in the plurality of sensors by the helical track in the second position.

12 Claims, 14 Drawing Sheets

(52) U.S. Cl.
CPC .... *A61M 5/31533* (2013.01); *A61M 5/31545* (2013.01); *A61M 5/31548* (2013.01); *A61M 5/31511* (2013.01); *A61M 5/31513* (2013.01); *A61M 5/31535* (2013.01); *A61M 5/31551* (2013.01); *A61M 5/31568* (2013.01); *A61M 2205/3306* (2013.01); *A61M 2205/3317* (2013.01); *A61M 2205/50* (2013.01); *G01D 5/2455* (2013.01)

(58) Field of Classification Search
CPC .......... A61M 5/31551; A61M 5/31568; A61M 5/3158; A61M 5/31585; A61M 2205/3306; A61M 2205/3317; A61M 2205/50; A61M 2205/6027; A61M 2205/6063; A61M 5/31501; A61M 5/31533; A61M 5/31535; A61M 5/31545; A61M 5/31553; A61M 5/3156; A61M 5/31561; A61M 5/31578; A61M 2205/52
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0123829 A1 | 5/2007 | Atterbury et al. | |
| 2009/0076460 A1 | 3/2009 | Nielsen et al. | |
| 2009/0275916 A1 | 11/2009 | Harms et al. | |
| 2011/0181301 A1 | 7/2011 | Nielsen et al. | |
| 2011/0270214 A1* | 11/2011 | Jorgensen | A61M 5/31551 604/500 |

FOREIGN PATENT DOCUMENTS

| | | |
|---|---|---|
| WO | 9938554 A1 | 8/1999 |
| WO | 9110484 A1 | 2/2001 |
| WO | 2006120182 A1 | 11/2006 |
| WO | 2013004844 A1 | 1/2013 |

OTHER PUBLICATIONS

International Preliminary Report on Patentability in Application No. PCT/EP2014/050469, dated Jul. 21, 2015, 8 pages.

* cited by examiner

|                          | Position '0'        | Position '1'        | Position '2'        |
|                          | zero dose dialled   | x dose units dialled | y dose units dialled |
|                          | First output: 1000001 | Second output: 0000011 | Third output: 0000110 |

| Contact 1 | 1 | 1 | 1 |
| Contact 2 | 0 | 0 | 0 |
| Contact 3 | 0 | 0 | 0 |
| Contact 4 | 0 | 0 | 0 |
| Contact 5 | 0 | 0 | 0 |
| Contact 6 | 0 | 0 | 1 |
| Contact 7 | 1 | 1 | 1 |
|           | 1 | 1 | 1 |
|           | 0 | 0 | 0 |
|           | 0 | 0 | 0 |
|           | 0 | 0 | 0 |
|           | 0 | 0 | 0 |
|           | 1 | 1 | 1 |
|           | 0 | 0 | 0 |
|           | 1 | 1 | 1 |
|           | 0 | 0 | 0 |
|           | 0 | 0 | 0 |
|           | 0 | 0 | 0 |
|           | 0 | 0 | 0 |
|           | 1 | 1 | 1 |
|           | 1 | 1 | 1 |
|           | 1 | 1 | 1 |

Seven contacts

PEN TYPE DRUG INJECTION DEVICE WITH DOSE ENCODER MECHANISM AND DOSE SETTING/DOSE DELIVERY MODE SWITCH

CROSS REFERENCE TO RELATED APPLICATIONS

The present application is a U.S. National Phase Application pursuant to 35 U.S.C. § 371 of International Application No. PCT/EP2014/050469 filed Jan. 13, 2014, which claims priority to European Patent Application No. 13151373.1 filed Jan. 15, 2013. The entire disclosure contents of these applications are herewith incorporated by reference into the present application.

FIELD OF INVENTION

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

According to an aspect of the present invention there is provided a drug delivery device comprising: a housing; a plurality of sensors; and a cylindrical member supported within the housing, the outer surface of said cylindrical member being provided with a helical track, the helical track comprising track segments of a first type and track segments of a second type, the first and second types of track segment being respectively capable of inducing first and second responses in the sensors; wherein: the helical track has a width dimension; the helical track includes across its width at least one track segment of the first type and at least one track segment of the second type at plural positions along the length of the helical track; the device is configured such that during a first phase of a drug delivery operation the helical track is moved axially, without rotation, relative to the plurality of sensors between a first position and a second position, and during a second phase of the drug delivery operation the track is moved helically relative to the plurality of sensors from the second position; and responses induced in the plurality of sensors by the track segments of the helical track are different in the first position compared to responses induced in the plurality of sensors by the helical track in the second position.

Advantageously, responses induced in the sensors can be used to determine an amount of drug delivered and/or dialled by the device in addition to whether the drug delivery device is in drug dispensing mode or dialling mode.

The plurality of sensors may be arranged to have a response induced in them by first and second pluralities of said track segments when the helical track is in the first and second positions relative to the sensors respectively.

At least one track segment in the first plurality of track segments may be of a different type compared to the track segments in the second plurality of track segments.

The device may be configured such that the helical track may be moved relative to the sensors along first and second helical paths that are axially offset relative to one another.

The device may be configured such that in use responses induced in the plurality of sensors by the track segments as the helical track moves along the first helical path are different to those induced in the plurality of sensors by the track segments as the helical track moves along the second helical path.

Advantageously, responses induced in the sensors can be used to determine an amount of drug delivered and/or dialled by the device in addition to whether the drug delivery device is in drug dispensing mode or dialling mode.

The device may be configured such that during the first phase of the drug delivery operation the helical track is moved axially, without rotation, relative to the plurality of sensors between a first position located on the first helical path and a second position located on the second helical path, and during the second phase of the drug delivery operation the helical track is moved along the second helical path.

The device may have eight sensors.

Advantageously, the enables up to 256 discrete positions of the cylindrical member to be uniquely encoded.

The helical track may comprise a first track segment of the first type at a first location on the width of the helical track for the whole of the length of the helical track, and a second track segment of the second type at a second location on the width of the helical track for the whole of the length of the helical track.

The first track segment may be able to induce a first response in a sensor when the helical track is in the first position relative to the sensors, and the second track segment may be able to induce a second response in said sensor when the helical track is in the second position relative to the sensors.

The device may further comprise a detector for detecting when a dose is being dialled and when a dialled dose has been fully dispensed, said detector being able to cause power to be supplied to the sensors when a dose is being dialled and to cause power not to be supplied to the sensors when a dialled dose has been fully dispensed.

Advantageously, this reduces power consumption of the drug delivery device.

The detector may comprise first and second parts of a two-part mechanism, wherein the first part is located on the cylindrical member, said detector being configured such that the first and second parts thereof only engage one another when a dose has not been dialled or a dialled dose has been fully dispensed.

The device may further comprise a processor configured to receive and interpret electrical signals from each of the sensors to determine the position of the cylindrical member relative to the housing.

The processor may be configured to determine a selected drug dose by searching a lookup table which provides a conversion between a position of the cylindrical member relative to the housing and a selected drug dose.

The processor may be configured to determine an operational mode of the drug delivery device by searching a lookup table which provides a conversion between a position of the cylindrical member relative to the housing and an operational mode of the drug delivery device.

BRIEF DESCRIPTION OF THE DRAWINGS

Embodiments will now be described, by way of example only, with reference to the accompanying drawings, in which:

FIG. 12 shows a graphical representation of the position-determining contacts 212a-212g in FIG. 9 (depicted as contacts 1 to 7) as they move over a coded strip 300;

FIG. 12a shows a numerical representation of the coded strip 300 in FIG. 11;

DETAILED DESCRIPTION

Figure 1:
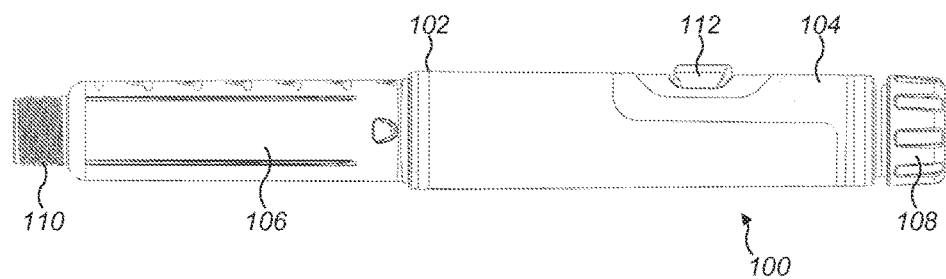
FIG. 1 shows an external view of a drug delivery device 100.

Referring firstly to FIG. 1, an external view of a drug delivery device 100 is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way that the drug cartridge is permanently contained within the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a dose delivery button (416 in FIG. 3) which must be depressed in order to deliver the set drug dose. The display 112 may be configured to display information concerning the drug dose which has been set and/or delivered. The display 112 may further show additional information, such as the actual time, the time of the last usage/injection, a remaining battery capacity, one or more warning signs indicating that a dialled dose has not been fully dispensed, and/or the like.

Figure 2:
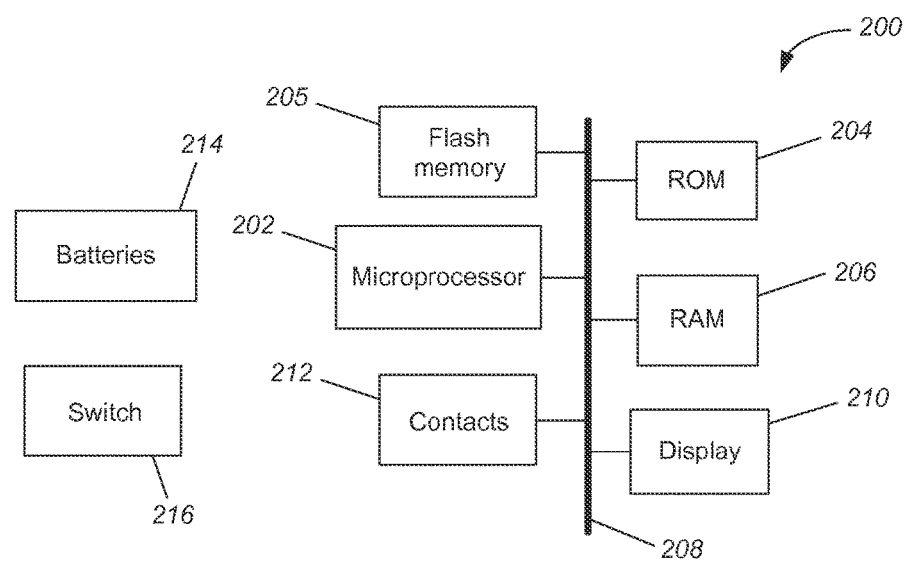
FIG. 2 shows a schematic diagram of some of the electronic components present in the drug delivery device 100 of FIG. 1.

Referring now to FIG. 2, a schematic diagram of electrical circuitry 200 forming part of the drug delivery device 100 is shown. The circuitry 200 comprises a processor 202, a non-volatile memory such as a ROM 204, a writable non-volatile memory such as flash memory 205, a volatile memory such as a RAM 206, a display 210, contacts 212 (described in more detail later on) and a bus 208 connecting each of these components. The circuitry 200 also comprises batteries 214 or some other suitable source of power for providing power to each of the components and a switch 216.

The circuitry 200 may be integral with the device 100. Alternatively, the circuitry 200 may be contained within an electronic module that can be attached to the device 100. In addition, the circuitry 200 may comprise additional sensors, such as optical or acoustical sensors. The circuitry 200 may comprise an audible alarm (not shown) which the processor 202 may control to sound an alarm when a dialled dose has not been fully dispensed.

The ROM 204 may be configured to store software and/or firmware. This software/firmware may control operations of the processor 202. The processor 202 utilises RAM 206 to execute the software/firmware stored in the ROM to control operation of the display 210. As such the processor 202 may also comprise a display driver. The processor 202 utilises the flash memory 205 to store determined amounts of dose dialled and/or determined amounts of dose dispensed, as will be described in more detail below.

The batteries 214 may provide power for each of the components including the contacts 212. The supply of electricity to the contacts 212 may be controlled by the processor 202. The processor 202 may receive signals from the contacts 212 and so could determine when the contacts are energised, and is configured to interpret these signals. Information may be provided on the display 210 at suitable times by operation of the software/firmware and the processor 202. This information may include measurements determined from the signals received by the processor 202 from the contacts 212.

A number of contacts 212 may be present in the device 100. In one embodiment, seven contacts 212 are present and may be addressed individually by the processor. In other envisaged embodiments more or less than seven contacts may be present. The contacts 212 may be mounted on an inner surface of the housing 102.

Dose Setting and Delivery Mechanism

Figure 3:
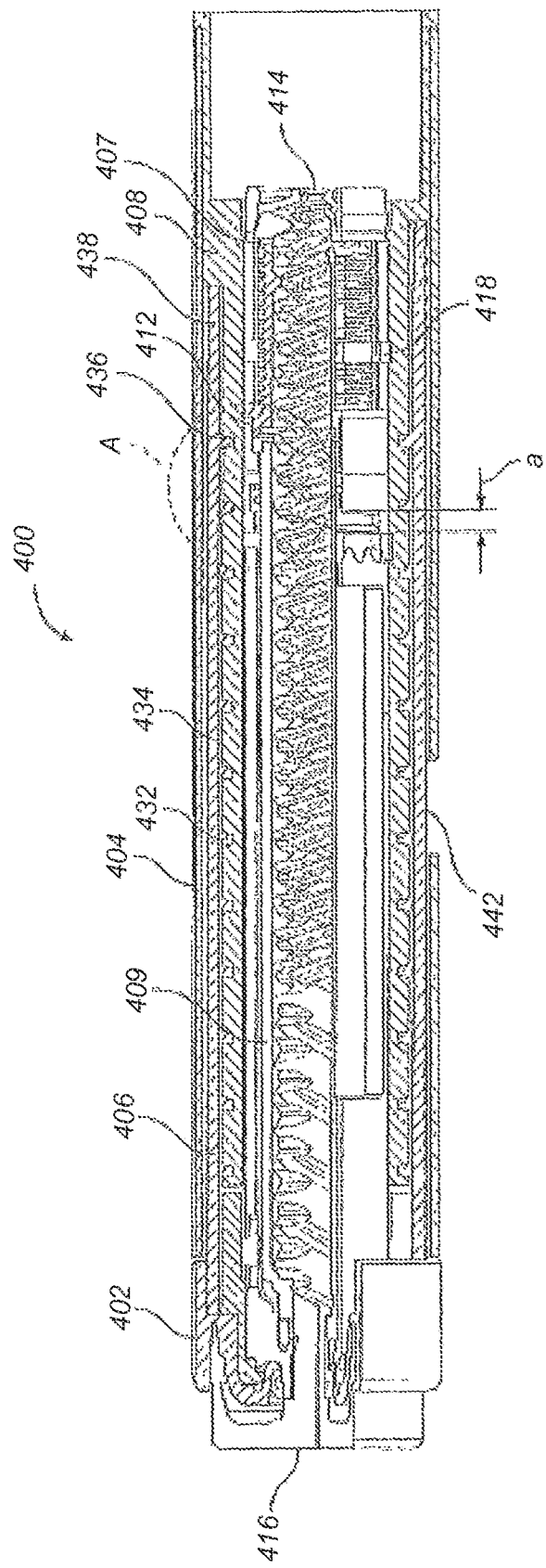
FIG. 3 shows a dose setting mechanism 400 of a drug delivery device 100.
Figure 4:
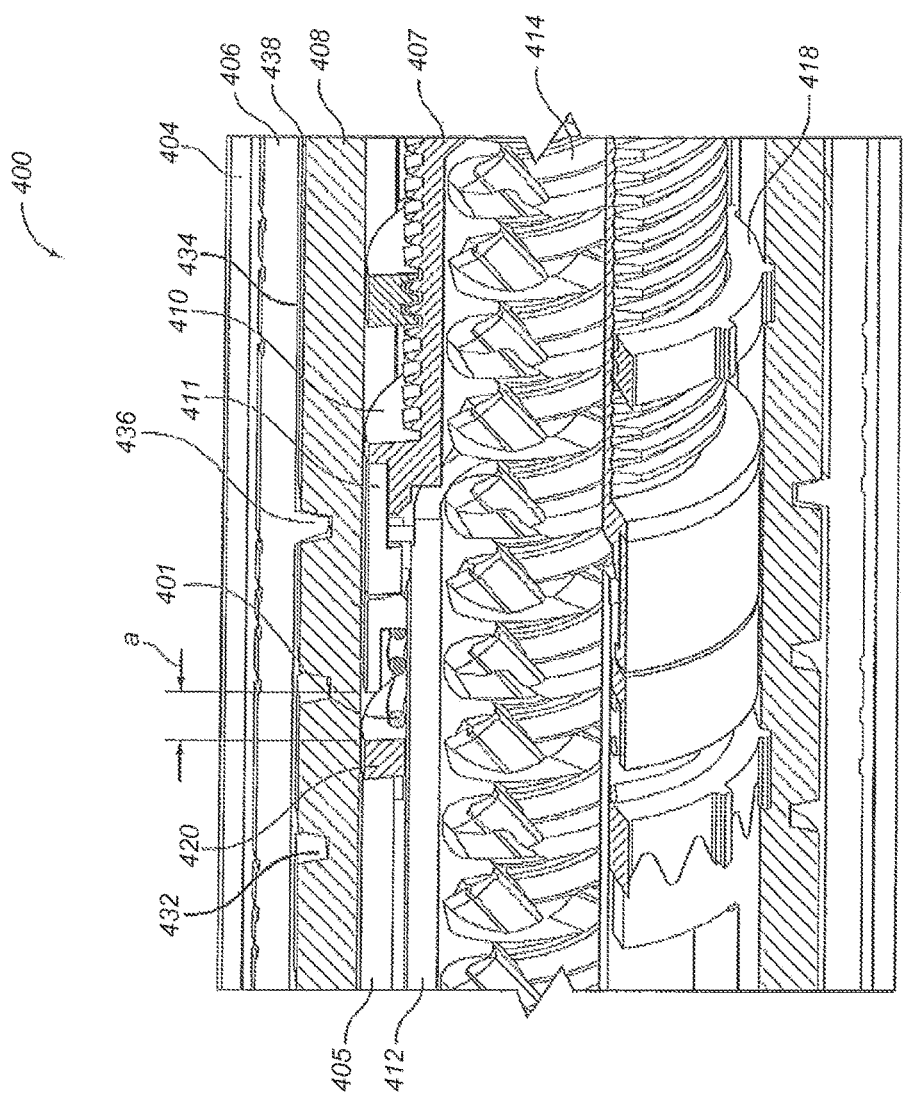
FIG. 4 shows detail of the dose setting mechanism 400 of FIG. 3.
Figure 5:
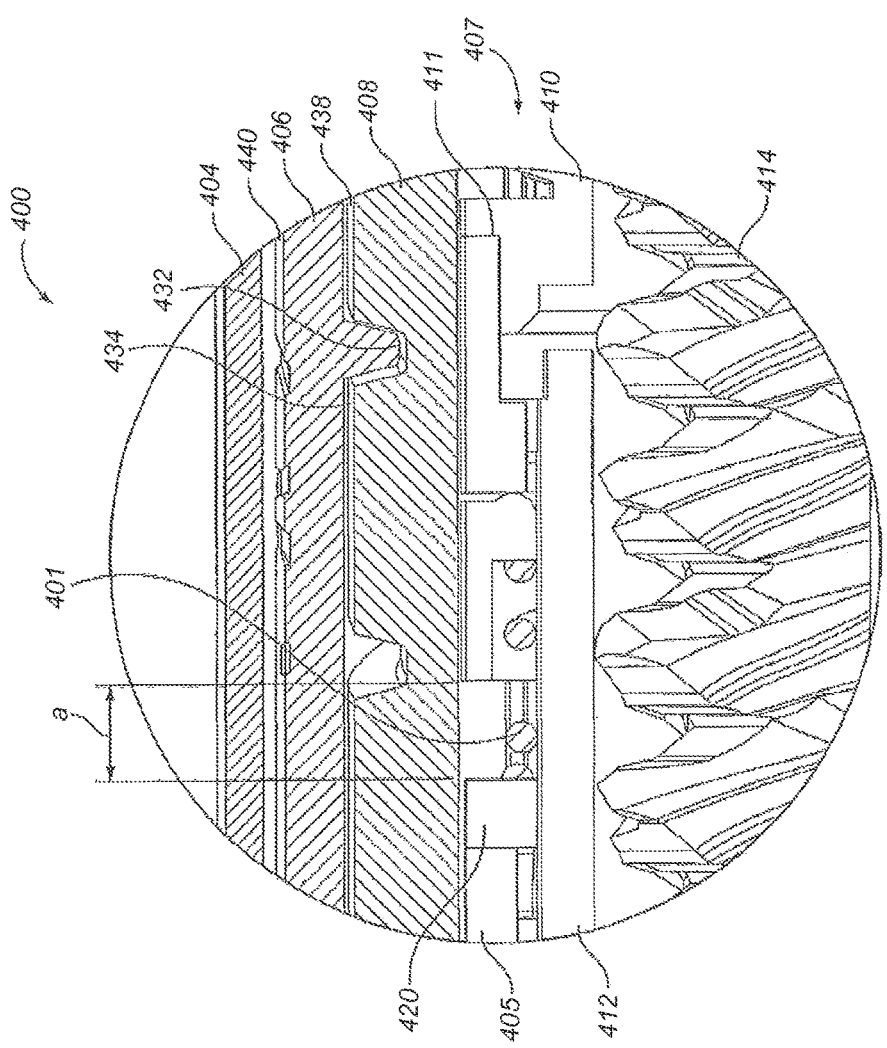
FIG. 5 shows a close up of the region marked 'A' in FIG. 3.

A fuller explanation of a dose setting and delivery mechanism capable of being supported within the first housing part 104 will now be given with reference to FIGS. 3 to 6. FIG. 3 is a cross-sectional view of a dose setting mechanism 400 of a drug delivery device 100. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and an encoded member or sleeve 406. These components may be hollow cylinders or sleeves arranged concentrically. The encoded member 406 is disposed between the outer and inner housings 404, 408. The inner housing 408 comprises a groove 432 provided along an external surface 434 of the inner housing 408. A groove guide 436 provided on an inner surface 438 of the encoded member 406 is rotatably engaged with this groove 432. The encoded member 406 has information encoded on its outer surface 440 (see FIGS. 8 and 13 for example) as will be described in more detail below. The encoded member 406 may be termed an encoder sleeve.

A dose dial grip 402 is located at a proximal end of the outer housing 404. The dose dial grip 402 is disposed about an outer surface of a proximal end of the encoded member 406. An outer diameter of the dose dial grip 402 may correspond to the outer diameter of the outer housing 404. The dose dial grip 402 is secured to the encoded member 406 to prevent relative movement between these two components. The dose dial grip 402 is represented in the external view of FIG. 1 by the rotatable dial 108. The dose dial grip 402 supports a dose delivery button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that may extend over at least a majority of a length of the spindle. Each groove form is effectively continuous over a number of turns. Each groove of the spindle may engage either a non-continuous helical groove form on a body portion or on a driver. Either or both a non-continuous thread form on a body and a driver may consist of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. The first driver portion 407 may comprise a first component part 410 and a second component part 411. Alternatively, the first driver portion 407 may be an integral component part.

With the dose setting mechanism 400, as a user dials a dose with the dose dial grip 402, the metal spring 401 is selected to be strong enough to maintain engagement of both clutched couplings: the clutched coupling between the clutch 405 and the encoded member 406 and clutched coupling between the first driver portion 407 and second driver portion 412. The encoded member 406 is coupled to the dose dial grip 402 such that when a user rotates the dose dial grip 402, the encoded member 406 also rotates. As the encoded member 406 is rotated in a first rotational direction, it moves axially in a proximal direction due to its threaded connection to the inner housing 408.

When the drug delivery device is being dispensed, the user applies an axial load to the dose delivery button 416 located at the proximal end of the mechanism 400. The dose delivery button 416 is axially coupled to the clutch 405 and this prevents relative axial movement. Therefore, the clutch 405 moves axially towards the cartridge end or the distal end of the dose setting mechanism 400. This movement disengages the clutch 405 from the encoded member 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose delivery button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. The outer surface of the dose limiter 418 and an internal surface of the inner housing 408 may be keyed together by way of splines. This prevents relative rotation between the dose limiter 418 and the housing 408 while allowing relative longitudinal movement between these two components.

Figure 6:
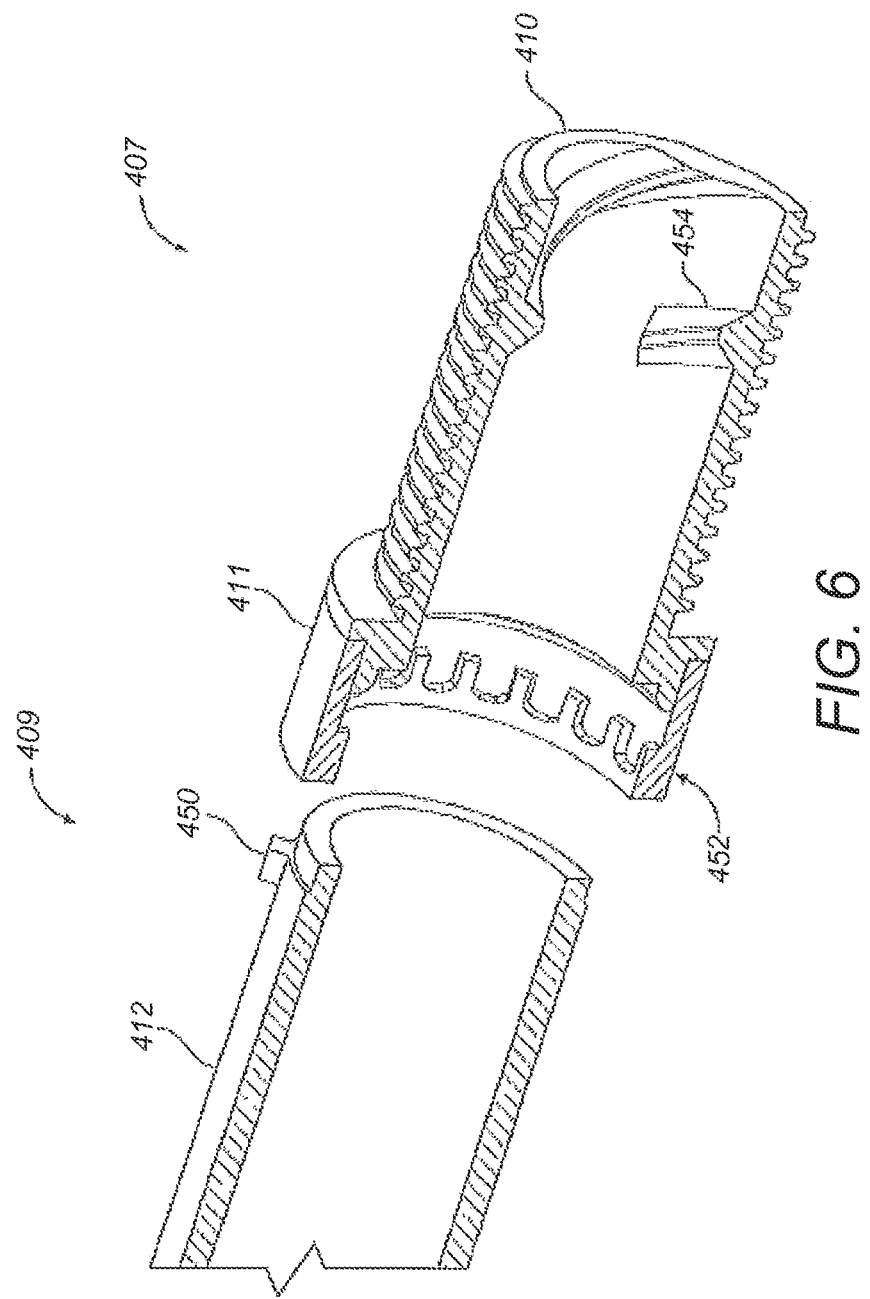
FIG. 6 is an exploded view showing details of a driver forming part of the dose setting mechanism 400 of FIGS. 3 to 5.

FIG. 6 shows in detail a first arrangement of the first driver portion 407 and the second driver portion 412 illustrated in FIGS. 3 to 5. As illustrated in FIG. 6, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove rather than a complete helical groove. One advantage of this arrangement is that it is generally easier to manufacture.

One advantage of this dose setting mechanism 400 utilizing the inner housing 408 is that the inner housing 408 can be made from an engineering plastic that minimizes friction relative to the encoded member 406 groove guide 436 and the groove 432. For example, one such engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the encoded member 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member rotates or locks to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the processor 202, ROM 204, flash memory 205, RAM 206, display electronics, contacts 212 and batteries 214 previously described. Alternatively, the contacts 212 may be supported at another position on the inner surface of the outer housing 404 and linked to the processor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the encoded member 406 in order to facilitate a determination of the rotational position of the encoded member 406, as will be described in more detail below.

The dose setting mechanism 400 illustrated in FIGS. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is decoupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This eventually decouples the first driver portion 407 and second driver portion 412.

This axial movement of the first driver portion 407 towards the second driver portion 412 results in certain advantages. For example, one advantage is that the metal spring 401 compresses and therefore closes the Gap 'a' illustrated in FIGS. 3-5. This in turn prevents the clutch 405 from disengaging from the clicker 420 or from the encoded member 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the encoded member 406. As a consequence, the encoded member 406 cannot rotate relative to the inner housing 404. If the encoded member 406 is prevented from rotating then, as the spindle 414 is retracted back into the dose setting mechanism 400 and thereby re-set, there is no risk of the encoded member 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver potion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

Dose Setting and Delivery Mechanism which Enables Axial Float

Figure 7:
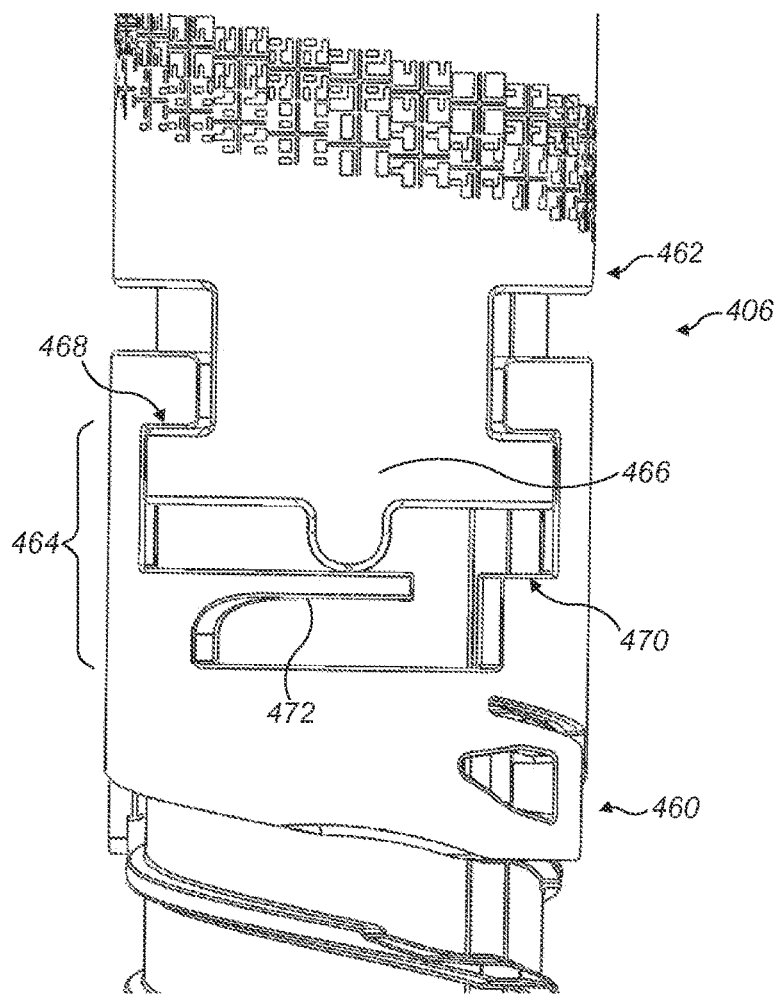
FIG. 7 shows an external view of a section of a two-part encoded member 406.

The foregoing merely concerns an example of one particular type of dose setting mechanism 400. A dose setting mechanism according to an aspect of the present invention differs from the one heretofore described in that the encoded member 406 comprises two parts. FIG. 7 depicts an envisaged arrangement of an encoded member 406 having two such parts. These two parts will be referred to hereafter as first and second encoded parts 460, 462 respectively.

The first encoded part 460 is provided with a guide 436 on its inner surface for rotatably engaging with the groove 432 provided along the external surface 434 of the inner housing 408 (see FIG. 4). The second encoded part 462 has information encoded on its outer surface. The first and second encoded parts 460, 462 are respectively provided with first and second parts 464, 466 of a two-part engagement mechanism. This engagement mechanism permits a defined amount of axial float between the first and second encoded parts 460, 462 while restricting relative rotational movement between such parts.

The first and second parts of the engagement mechanism may respectively comprise a socket 464 and an arm 466 which is slidably received in said socket 464. As shown in FIG. 7 the socket 464 defines front and rear surfaces 468, 470 between which the arm 466 can slide back-and-forth along the major axis of the first housing part 104. Flush engagement of the arm 466 with side surfaces of the socket 464 prevents relative rotational movement between the first and second encoded parts 460, 462.

Relative axial movement between the first and second encoded parts 460, 462 is permitted against a bias. In particular, the first and second encoded parts are biased in a direction away from one another. This may be achieved by utilising a spring 472 which biases the arm 466 into contact with front surfaces 468 of the cavity 464 (as in FIG. 7). Such a spring may comprise part of the first encoded part 460, alternatively however the spring may be a separate element. In either case forcing the second encoded part 462 towards the first encoded part 460 compresses the spring 472 up until the point at which the arm 466 engages rear surfaces 470 of the cavity 464.

Figure 7A:
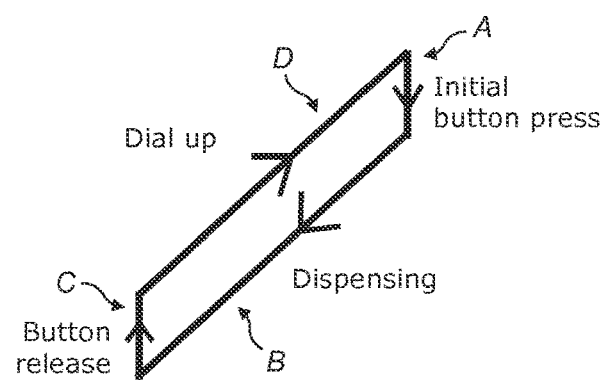
FIG. 7a depicts the various movement stages of an encoded member 406.

When a drug delivery device 100 is being used to dispense a drug, as has already been mentioned, a user applies an axial load to the dose delivery button 416 located at the proximal end of the mechanism 400. This causes the encoded member 406 to rotate when the clutch 405 is moved in the direction of the force applied to the dose delivery button 416 In the arrangement depicted in FIG. 7 however, before the encoded member 406 starts to rotate the first and second encoded parts 460, 462 thereof are moved towards one another so that the arm 466 is brought into engagement with rear surfaces 470 of the cavity 464. In other words, the first and second encoded parts 460, 462 are moved axially relative to one another (movement stage A in FIG. 7a). This movement causes the arm 466 to compress the spring 472 until the arm 466 comes into contact with rear surfaces 470 of the cavity 464. Only once this has occurred is the encoded member 406 capable of rotating upon further movement of the dose delivery button 416 relative to the housing 102 during dispense (movement stage B in FIG. 7a).

After an amount of drug has been dispensed, a user stops pressing the dose delivery button 416. The first and second encoded parts 460, 462 thus no longer are pushed towards one another such that the spring 472 relaxes and moves the arm 466 back into contact with front surfaces 468 of the cavity 464. This moves the first encoded part 460 and the second encoded part 462 (and thus the code provided thereon) back into their original positions relative to one another before the dispense operation occurred. In other words, relaxation of the spring 472 causes the first and second encoded parts 460, 462 to move axially relative to one another in an opposite direction to when the dose delivery button 416 was pressed (movement stage C in FIG. 7a). As will later be described in more detail, selecting a dose to be dispensed by twisting dial 108 causes the encoded member 406 to rotate in an opposite direction to that which it rotates during dispense (movement stage D in FIG. 7a).

It will be appreciated that in other arrangements the first and second parts of the two-part engagement mechanism may be reversed. In particular, the first part 464 of said two-part engagement mechanism may be located on the second encoded part 462, and the second part 466 of said two-part engagement mechanism may be located on the first encoded part 460. In particular, the cavity 464 and spring 472 may be located on the second encoded part 462 and the arm 466 may be located on the first encoded part 460.

Translational axial float of code provided on the encoded member 406 may be achieved in ways other than by utilising a two-part encoded member 406. For example, instead of having a two-part encoded member 406 a dose setting mechanism 400 may instead have a two-part inner housing 408 for example, said two-parts having an axial float between them. Such two parts may also be connected via a two-part engagement mechanism of the kind depicted in FIG. 7 although any other mechanism permitting some axial movement between the two parts while restricting relative rotational movement may be used. In such an arrangement, pressing the dose delivery button 416 causes both parts of the inner housing 408 to move axially towards one another a predefined amount. This thereby causes the encoded member 406 (and thus code located thereon) to move axially with the housing 408 before the encoded member 406 is caused to rotate during a drug dispensing operation.

The dose setting mechanisms 400 described above which permit axial float are merely examples of mechanisms suitable for implementing the present invention. It will be apparent to the skilled person that other mechanisms may also be suitable. In particular, for the purpose of describing envisaged embodiments of the present invention, any suitable type of dose setting mechanism 400 may be used. Information provided on the encoded member 406 is able to be moved both axially (a predefined distance) and rotationally relative to contacts 212 (see FIG. 2) or, in other words, such information is capable of being rotated about two axially off-set helical paths depending on whether the drug delivery device 100 is in dialling mode or dispensing mode. A person skilled in the art is free to decide which type of dose setting and delivering mechanism 400 to use in order to permit such movement.

First Embodiment

Figure 9:
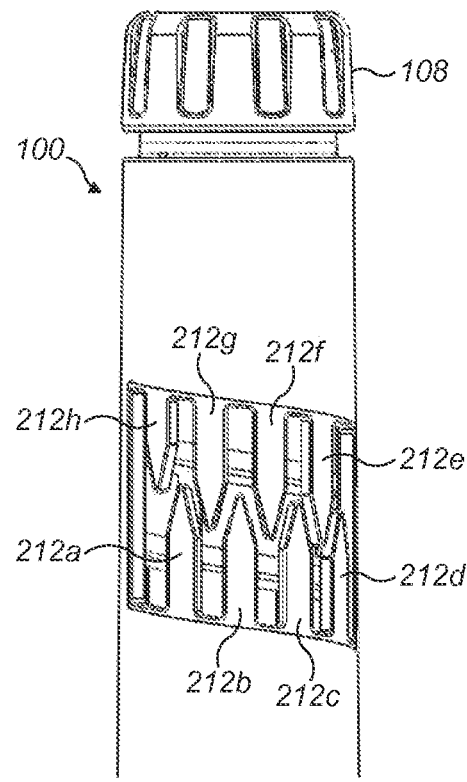
FIG. 9 shows an external view of part of a drug delivery device 100 according to a first embodiment of the present invention.

In view of the foregoing it will be appreciated that a user twists the rotatable dial 108 (see FIG. 1) to select an amount of dose to be dispensed from a drug cartridge. This causes the encoded member 406 to rotate and translate axially (longitudinally) relative to the housing 102. In particular, the encoded member moves slightly away from the housing as shown in FIG. 9 for example. By analysing information provided on the outer surface 440 of the encoded member 406 the extent of rotation of the dial 108, and thus the amount of dose dialled, can be determined. Furthermore, a user presses the dose delivery button 416 (see FIG. 3) to dispense an amount of dose from within a drug cartridge once a dose has been dialled. Pressing the dose delivery button 416 causes at least the section of encoded member 406 provided with information on it's outer surface to move axially (without rotating) a predefined distance in a direction away from the dose delivery button 416. Once this has occurred, upon continuing to press the dose delivery button 416 the encoded member rotates and thus moves helically in a direction away from the dose delivery button 416 back into the housing 102. By analysing information provided on the outer surface 440 of the encoded member 406 as it rotates, how far the dose delivery button 416 has been pushed and thus the amount of dose dispensed can also be determined. How this is achieved will now be described.

Figure 8:
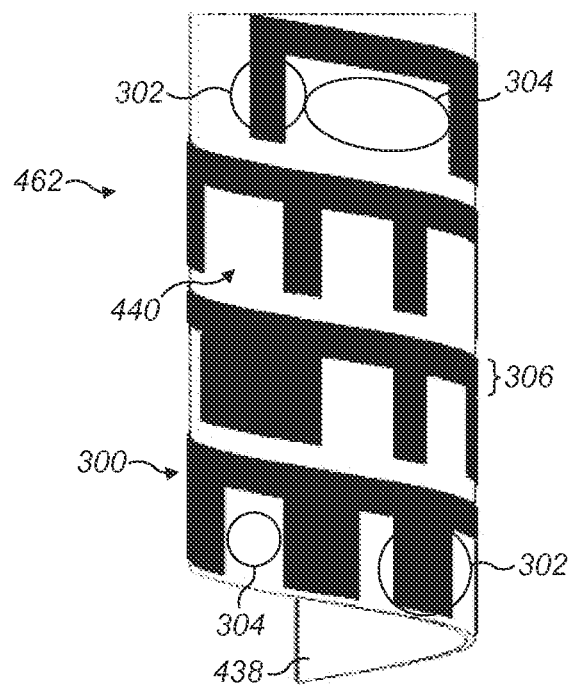
FIG. 8 shows part of an encoded member 406 according to a first embodiment of the present invention.

FIG. 8 illustrates part of an encoded member 406 according to a first embodiment of the present invention. The part depicted may comprise a single section of a two-part encoded member, thereby corresponding to the second part 462 illustrated in FIG. 7. Alternatively the section of encoded member in FIG. 8 may form part of a one-part encoded member. In order for such a one-part encoded member to have a degree of axial float it should be used in a drug delivery device configured to permit such movement, for example a device provided with a two-part inner housing 108. As mentioned earlier, any suitable configuration of the dose setting mechanism 400 may be used. Information provided on the outer surface of the encoded member 406 is able to be moved both axially (a predefined distance, without rotating) and rotationally. In other words such information is capable of being rotated about two axially off-set helical paths. A person skilled in the art is free to decide which dose setting and delivering mechanism they want to use to permit such movement.

The encoded member section 406 depicted in FIG. 8 is provided on its outer surface 440 with a helical track 300 according to a first embodiment. FIG. 8 shows that the helical track comprises a series of conductive segments 302 (shown in black) that are electrically coupled to one another by a power line 306 (also shown in black). Non-conductive or insulating segments 304 (shown in white) are defined in the space between respective conductive segments 302. It should also be noted that in the present embodiment the area located on the encoded member 406 which is labelled D in FIG. 10, and is electrically insulating, also comprises part of the helical track 300. In particular the area labelled D in FIG. 10, which extends helically around the encoded member 406 adjacent the power line 306, also comprises a non-conductive or insulating segment 304 of the helical track 300.

The helical track 300 may be formed on the outer surface 440 of the depicted encoded member section 406 by wrapping a metallic strip around the encoded member. Such a metallic strip may have a non-conductive backing to support the metallic layer. The non-conductive backing may have an adhesive on the reverse side for securing the strip to the outer surface 440 of the encoded member 406. The helical track 300 may alternatively comprise conductive ink printed onto a non-conductive substrate. This non-conductive substrate may be the encoded member 406 itself or a secondary substrate which is subsequently attached to the encoded member 406.

A drug delivery device 100, according to a first embodiment, is provided with electrical contacts 212a-212h that engage the helical track 300 at different locations along the length of the track 300 as in FIG. 9 (the display mount 112 not being shown). The pitch of the helix along which the contacts 212a-212h are formed is the same as the pitch of the helix of the helical track 300, which is the same as the pitch of the threads that constrain movement of the encoded member 406 relative to the inner housing 408.

Advantageously, seven contacts 212a-212g are arranged around the encoded member 406 so that for a given rotational position of the encoded member 406, some of the contacts 212a-212g engage conductive segments 302 whereas the other such contacts engage non-conductive segments 304. In particular, the helical track 300 and contacts 212a-212g are arranged such that for each rotational position of the encoded member 406, at least two contacts 212a-212g are in engagement with conductive segments 302. Such contacts 212a-212g may be angularly separated by an amount equal to one bit of the code represented by the helical track 300, e.g. 15 degrees, relative to one another along the length of the helical track 300 for example.

A dedicated eighth contact 212h is also provided for engaging the power line 306 of the helical track 300. This eighth contact 212h is configured to remain in engagement with the power line 306 when the drug delivery device 100 is in dialling mode. In other words, when a dose is being dialled and the encoded member 406 rotates and thus moves axially relative to the housing 102, the eighth contact 212h remains in engagement with the power line 306. As such, the eighth contact 212h will be referred to hereafter as the power line contact 212h.

In dispense mode, as has already been mentioned, a user presses the dose delivery button 416 in order to dispense an amount of drug from a cartridge. Due to the axial float permitted by the drug delivery device (regardless of how such movement is enabled), upon pressing the dose delivery button 416 the helical track 300 is shifted axially (without rotating) in a direction away from the dose delivery button 416. Once the helical track 300 has been shifted a predefined amount, further pushing the dose delivery button 416 causes a drug dose to be dispensed as the encoded member 406 is caused to move helically (by simultaneous rotation and axial movement) within the housing. The extent to which the encoded member 406 rotates corresponds to the amount of dose dispensed.

In view of the foregoing paragraph, reference will now be made to FIG. 10. It should be remembered that when the encoded member 406 is caused to rotate, the encoded member 406 moves axially within the housing 102 due to threaded engagement of groove guide 436 with the inner housing 108. In dialling mode, the section of helical track 300 labelled "A" sweeps across the seven contacts 212a-212g when the encoded member 406 is rotated. The distance which the section of helical track 300 labelled "A" sweeps across the seven contacts 212a-212g corresponds to the dose dialled. Furthermore, the section of helical track 300 labelled "B" sweeps across the power line contact 212h during dialling.

In dispensing mode, after the helical track 300 has been shifted relative to the contacts 212a-212h due to the aforementioned axial float, the section of helical track 300 labelled "C" sweeps across the seven contacts 212a-212g when the encoded member is rotated by an amount corresponding to the dose dispensed. Furthermore, the section of helical track 300 labelled "D" sweeps across the power line contact 212h during dispense.

Figure 11:
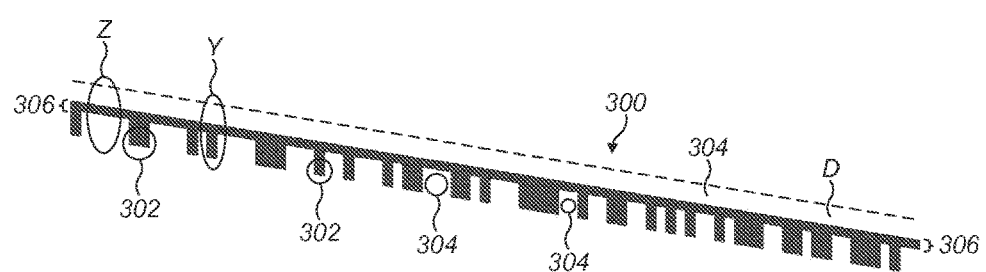
FIG. 11 shows a coded strip 300 suitable for use in manufacturing the encoded member, part of which is shown in FIG. 8.

FIG. 11 illustrates the helical track 300 (which could comprise a metallic strip) in unwrapped form. The conductive segments 302 (shown in black) are electrically coupled to one another via a power line 306 (also shown in black). It will therefore be appreciated that applying a voltage to one of the conductive segments 302 causes all of the conductive segments 302 to be energised by virtue of their connection to the power line 306.

Looking back at FIG. 9 the contacts 212a-212h are shown supported in the recess 442 (the display mount 112 not being shown). The contacts 212a-212h may be biased against the outer surface 440 of the encoded member 406 in order to provide a stable electrical connection with the helical track 300. Additionally, the contacts 212a-212h are inclined relative to the longitudinal axis of the device 100 by the same degree as the pitch of the helical track 300. The pitch of the helical track 300 is the same as the pitch of the groove guide 436 of the encoded member 406 which engages with the inner housing groove 432. Therefore, when the encoded member 406 rotates and moves axially within the housing 102, the helical track 300 is always positioned directly underneath the seven contacts 212a-212g (but not always the power line contact 212h as already outlined). More specifically the section of helical track 300 comprising the conductive and non-conductive segments 302, 304 along its length is always positioned directly underneath the seven contacts 212a-212g.

The processor 202 is capable of determining the extent of rotation of the encoded member 406, and thus an amount of dose dialled or dispensed, by analysing which of the seven contacts 212a-212g are in engagement with conductive sections of the helical track. How this is achieved will now be explained. In view of their function, contacts 212a-212g will be referred to hereafter as position-determining contacts.

The processor 202 is configured to address each of the seven contacts 212a-212h individually. The processor 202 is also configured to control the provision of a voltage signal from the batteries 214 to the position-determining contacts 212a-212g. However, when the batteries 214 provide a signal having a voltage to one of the position-determining contacts 212a-212g, certain others of the contacts (including the power line contact 212h) may also be energised by virtue of being in electrical connection with the energised contact via the power line 306. Thus, the batteries may provide a voltage to a first of the contacts (for example, contact 212a) and the processor 202 may detect signals from each of the other contacts that are energised due to being in electrical connection with the first contact 212a through the power line 306. Since the processor 202 can address the position-determining contacts 212a-212g individually, it is able to apply a signal to different such contacts, each time monitoring signals from the other contacts.

It may be that the drug delivery device 100 is an insulin pen type injection device. As such, users may need to set an insulin dose of between 1 and 80 International Units. Advantageously, the helical track 300 utilised in conjunction with seven position-determining contacts 212a-212g provides a seven bit encoding system. This allows $2^7=128$ discrete rotational positions of the encoded member 406 to be uniquely encoded. Thus the full 0-80 unit dialable dose for an injection device can be absolutely encoded with redundant positions available.

The seven bit encoding system is provided by arranging the foregoing conductive and non-conductive segments 302, 304 of the helical track 300 such that they form a type of code. FIG. 12 illustrates how the seven position-determining contacts 212a-212g of the present embodiment (depicted as contacts 1-7) move into and out of engagement with conductive and non-conductive segments 302, 304 of the helical track 300 when the encoded member 406 is moved rotationally (and thus axially via threaded engagement of groove guide 436 with the inner housing 108) relative to the housing 102.

A code digit of "1" denotes that a contact engages a conductive segment 302 whereas a code digit of "0" denotes that a contact engages a non-conductive segment 304. From FIG. 12 it will be apparent that when the seven contacts 212a-212g move along the helical track 300 (upon rotation and thus axial movement of the encoded member 406) the contacts come into engagement with various unique configurations of conductive and non-conductive segments 302, 304. In particular, in the illustrative example of the present embodiment, the contacts encounter 81 unique configurations of conductive and non-conductive segments 302, 304 as they move along the helical track 300.

FIG. 12a depicts a numerical representation of the track 300 in FIG. 11. From FIG. 12a the 81 unique seven bit binary codes associated with the 81 unique rotational positions of the encoded member 406 can be determined.

When a user of the device 100 twists the rotatable dial 108 (see FIG. 9) to select or dial in a drug dose, the processor 202 may be activated and may be controlled by software stored in the ROM 204 to execute a check on the position-determining contacts 212a-212g to determine the absolute rotational position of the encoded member 406, and hence the drug dose which has been dialled. The processor 202 may similarly determine the number of drug units which have been delivered.

The process of determining a dialled dose will now be described. In order to determine a drug dose which has been dialled, the processor 202 first causes the batteries 214 to apply a voltage to a first contact (for example, contact 212a) and then determines which of the remaining position-determining contacts 212b-212g are energised. It should be remembered that in the present embodiment, for each rotational position of the encoded member 406 at least two position-determining contacts 212a-212g engage a conductive segment 302 of the helical track 300. Thus when a voltage is applied to the first contact 212a, if any of the remaining six contacts 212b-212g are energised then both the first contact and the other energised contacts are associated with a code value of "1". This denotes that such contacts are in engagement with a conductive segment 302 of the track 300. The contacts that were not energised are associated with a code value of "0". This denotes that such contacts are in engagement with a non-conductive segment 304 of the track 300.

Analysing which position-determining contacts are associated with a code value of "1" and which are associated with a code value of "0" the processor 202 can determine the unique seven bit binary code associated with the absolute rotational position of the encoded member 406. The processor 202 can then use the seven bit binary code to determine the dialled dose. This may be achieved by the processor 202 upon searching a lookup table stored in the ROM 204, the lookup table providing a conversion from the seven bit binary code result to a dose unit dialled.

If however, when a voltage is applied to the first contact (for example contact 212a) none of the other position-determining contacts 212b-212g are determined to be energised then the processor 202 instead applies a voltage to another one of such contacts (for example, the second contact 212b). The processor 202 then determines whether any of the other position-determining contacts are energised upon applying a voltage to the second contact 212b. This process is repeated for respective position-determining contacts until at least one of the seven contacts 212a-212g is detected as being energised upon application of a voltage to another one of those contacts. When this is detected as taking place the processor 202 uses the seven bit binary code associated with the absolute rotational position of the encoded member 406 to determine the dialled dose in the manner heretofore described. In particular the processor 202 compares the seven bit binary code with a lookup table to determine the dialled dose amount.

As for the power line contact 212h, since the device 100 is in dialling mode the power line contact 212h is also energised and associated with a code value of "1" upon applying a voltage to a position-determining contact that is in engagement with a conductive segment 302 of track. In other words, when the seven bit binary code associated with the absolute rotational position of the encoded member 406 is determined, the power line contact 212h is energised. Detecting this enables the processor to determine that the device 100 is in dialling mode.

As an illustrative example, before dialling a dose by twisting the rotatable dial 108 the encoded member 406 may be in a position associated with the code depicted on the left-hand side in FIG. 12. In such a "0" position (i.e. the zero dose dialled position) the processor 202 detects the seventh position-determining contact 212g (in addition to the power line contact 212h) to be energised when a voltage is applied to the first contact 212a. This is because in position "0", of the seven position-determining contacts 212a-212g, only the first and seventh such contacts 212a, 212g engage conductive segments 302 of helical track 300 whereas the other such contacts 212b-212f engage non-conductive segments 304. In effect the binary result "1000001" is read by the processor 202. From this the device 100 is determined by the processor 202 to be in the zero dose dialled configuration upon consulting a lookup table. This is because in such a lookup table a dialled dose amount of "zero dose units" is associated with the binary code value "1000001". A dialled dose amount of zero may be shown on the display 210 to a user of the drug delivery device 100.

Upon dialling a dose by twisting the rotatable dial 108 the encoded member 406 may be moved into a position associated with the code depicted on the right-hand side in FIG. 12 denoted as position "2". In this configuration no additional contacts are determined by the processor 202 to be energised when a voltage is applied to any of contacts one to four 212a-212d. However, upon applying a voltage to the fifth position determining contact 212e the processor 202 detects the sixth position-determining contact 212f (in addition to the power line contact 212h) as being energised. This is because in position "2", of the seven position-determining contacts 212a-212g, only the fifth and sixth contacts 212e, 212f engage conductive segments 302 of the helical track 306. In effect the binary code "0000110" is read by the processor 202 and the device is detected as being in dialling mode. From this the processor 202 can determine that Y dose units have been dialled upon consulting the aforementioned lookup table. This is because in such a lookup table a dialled dose amount of Y dose units is associated with binary code value "0000110". A dialled dose amount of Y dose units may be shown on the display 210 to a user of the drug delivery device 100.

It will be appreciated that in other arrangements the code defined by the helical track 300 may have a different configuration, in particular it may define a different combination of "0"s and "1"s to that used in the above illustrative example.

In addition to (or instead of) determining a dialled dose, the device 100 may be configured to determine an amount of dose that has been dispensed. For example, when an amount of dose has been dispensed the processor 202 may determine the position of the encoded member 406 relative to the housing 102 in the foregoing manner i.e. by determining the seven bit binary code associated with the absolute rotational position of the encoded member 406 and determining the dose amount associated with such a binary code from a lookup table.

Figure 10:
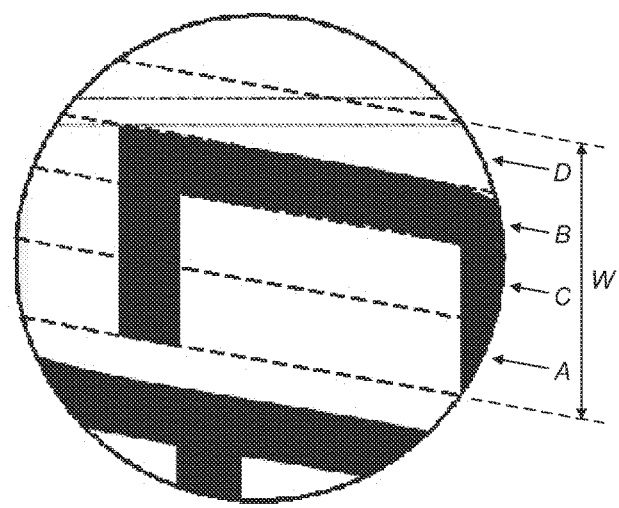
FIG. 10 shows a magnified view of part of the helical track 300 shown in FIG. 8.

The difference is that when the drug delivery device 100 is in dispensing mode the processor 202 determines the extent of rotation of the encoded member 406 by analysing which of the position-determining contacts 212a-212g engage conductive segments 302 of track 300 along the section labelled "C" in FIG. 10 (instead of along the section labelled "A" which occurs in dialling mode). Furthermore, in dispensing mode the translational shift of the helical track 300 relative to the contacts 212a-212h provides that the power line contact 212h is no longer in engagement with the power line 306. Instead, the power line contact 212h engages the non-conductive section of helical track labelled "D" in FIG. 10. Thus the power line contact 212h is not energised upon applying a voltage to any of the position determining contacts 212a-212g. This enables the processor 212 to determine that the device 100 is in dispensing mode. In particular not detecting the power line contact 212h as being energised when the seven bit binary code associated with the rotational position of the encoded member 406 is determined indicates that the device 100 is in dispensing mode.

The processor 202 may determine the drug dose which has been dispensed (or is yet to be dispensed, if any) by subtracting a remaining drug dose from an initially dialled drug dose. The display 210 may be used to show the dose amount yet to be dispensed if a user does not dispense the full amount of a dialled dose.

Having determined the drug dose which has been dispensed, the processor 202 may store the result in the flash memory 205. As mentioned above the display 210 may be controlled to display the result of the dispensed dose determination. The display 210 may show the result of the dispensed dose determination for a predetermined time, for example 60 seconds. Alternatively or in addition, the dispensed dose history may be retrieved electronically from the flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Further envisaged arrangements of the first embodiment described herein will now be briefly outlined.

Although a seven bit coding system has been described, the first embodiment is equally applicable for any number of position-determining contacts greater than three, in other words at least contacts 212a-212d as well as the power line contact 212h. The seven bit system is advantageous since it allows the full 0-80 unit dose range to be absolutely encoded.

The processor 202 may implement the process of checking the contacts 212a-212h while the encoded member 406 is actually rotating, i.e. while the device 100 is actually being dialled or is being used to dispense a substance. Alternatively the checking process may only be performed when the processor 202 detects that the encoded member 406 has been in a certain position for a predetermined amount of time (for example 100 milliseconds), thereby indicating that the device 100 has been dialled or dispensed an intended amount by a user.

Also, the device 100 may be configured so that the helical track 300 shifts the other way to that described in connection with FIG. 10. For instance the device 100 may be configured such that in dialling mode, the section of helical track 300 labelled "C" in FIG. 10 sweeps across the seven contacts 212a-212g and the section of helical track 300 labelled "D" sweeps across the power line contact 212h. In such an arrangement, when the device is in dispensing mode the section of helical track 300 labelled "A" sweeps across the seven position-determining contacts 212a-212g and the section of helical track 300 labelled "B" sweeps across the power line contact 212h.

Second Embodiment

Figure 13:
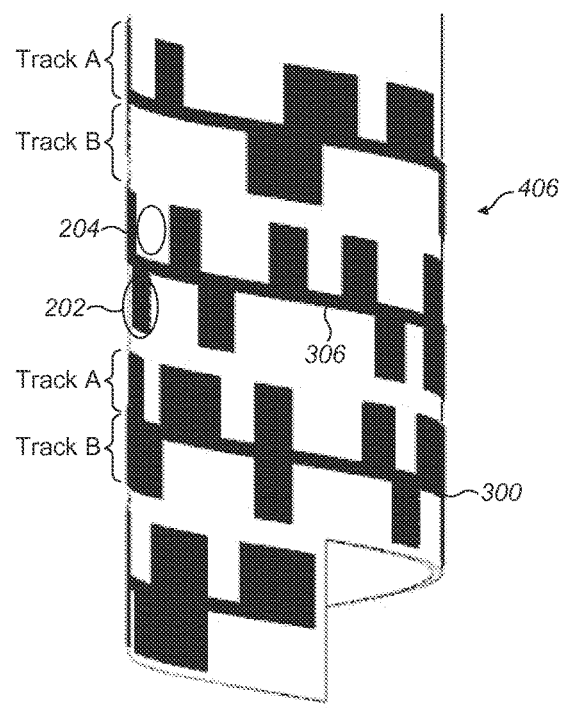
FIG. 13 shows an external view of part of a drug delivery device 100 according to a second embodiment of the present invention.
Figure 14:
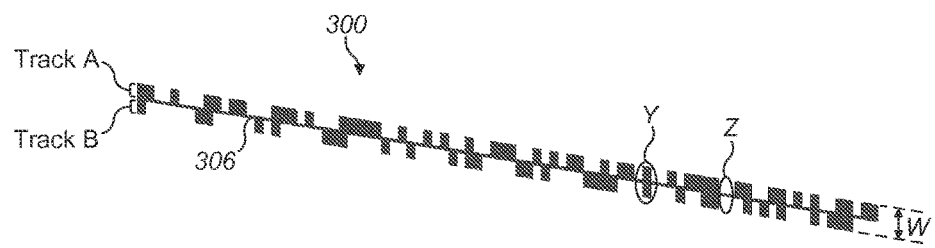
FIG. 14 shows a coded strip 300 suitable for use in manufacturing the encoded member, part of which is shown in FIG. 13.

FIG. 13 illustrates part of an encoded member 406 according to a second envisaged embodiment of the present invention. This encoded member 406 differs from the one depicted in FIG. 8 in that the helical track 300 has a different configuration. In particular the helical track 300 of the present embodiment has two series of conductive and non-conductive segments 302, 304, one series on each side of the power line 306. Such conductive and non-conductive segments 302, 304 define a different code on either side of the power line 306. The sections of track 300 defining these two codes are referred to hereafter as track-A and track-B. FIG. 14 depicts the helical track 300 in unwrapped form.

In the present embodiment an encoded member 406 is positioned in a drug delivery device 100 such that in dialling mode (when a dose is dialled) track-A is analysed by a series of contacts 212. This allows the absolute rotational position of the encoded member 406, and thus an amount of dose dialled, to be determined from track-A. Like in the foregoing embodiment, when the device 100 transitions between dialling and dispensing mode at least the section of encoded member 406 provided with the helical track 300 undergoes a translational shift relative to the contacts 212. As such, in dispensing mode track-B is analysed by the contacts 212 to determine the absolute rotational position of the encoded member 406 and thus an amount of dose dispensed.

Eight electrical contacts 212a-212h may be used with the dual-code helical track 300 depicted in FIG. 13, thereby forming an eight bit encoding system. This enables up to $2^8=256$ discrete positions of the encoded member 406 to be uniquely encoded. Thus the full 162 discrete positions of an encoded member within an insulin injection device configured to inject up to 80 International Units of insulin can be absolutely encoded with redundant positions available. Such encoded member positions include those associated with 0-80 International Units of dose in dialling mode and those associated with 0-80 International Units of dose in dispensing mode. How this is achieved will now be described.

Since the above mentioned contacts 212a-212h are used to determine the absolute rotational position of the encoded member 406 they will be referred to hereafter as position-determining contacts. Advantageously, the position-determining contacts 212a-212h are arranged around the encoded member 406 so that for a given rotational position of the encoded member 406, some of the contacts 212a-212h engage conductive segments 302 whereas the other contacts engage non-conductive segments 304.

The drug delivery device 100 may be configured such that during dose dialling at least two contacts 212a-212h engage conductive segments 302 of track-A in each rotational position of the encoded member 406. The other such contacts engage non-conductive segments 304 of track-A. In dispensing mode however at least two contacts 212a-212h engage conductive segments 302 of track-B in each rotational position of the encoded member 406. The other such contacts engage non-conductive segments 304 of track-B.

The respective codes defined by track-A and track-B will now be further described. It will be appreciated from FIG. 14 that tracks A and B have different combinations of conductive and non-conductive segments 302, 304. As a result the codes defined by these two tracks are associated with different combinations of "0"s and "1"s.

Figures 15, 16:
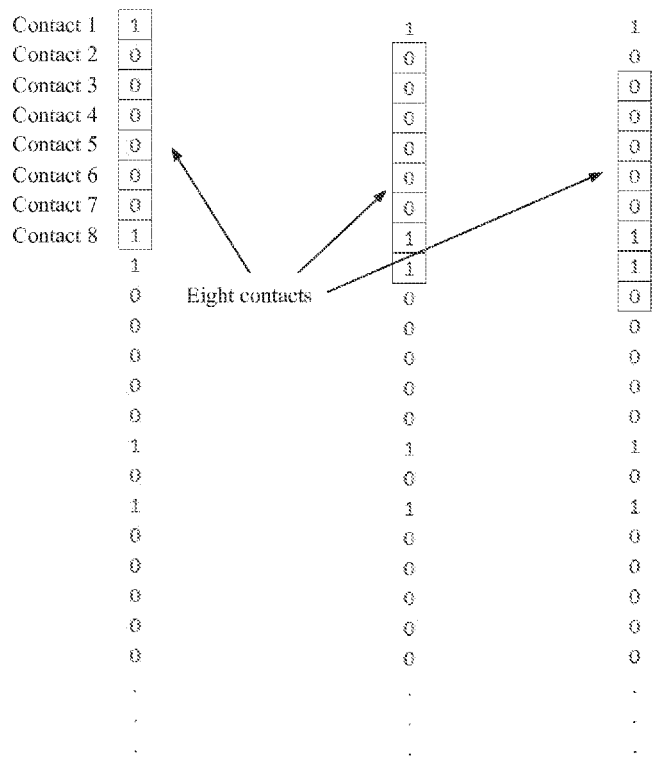
FIG. 15 shows a graphical representation of eight position-determining contacts 212a-212h (depicted as contacts 1 to 8) as they move over track-A in FIG. 13.
FIG. 16 shows a numerical representation of track-A in FIG. 14.

FIG. 15 (which corresponds to FIG. 12) illustrates how the eight position-determining contacts 212a-212h of the present embodiment (depicted as contacts 1-8) move into and out of engagement with conductive and non-conductive segments 302, 304 of track-A when the encoded member 406 is moved rotationally relative to the housing 102 in dialling mode. Note that such rotational movement also causes the encoded member 406 to move axially due to the threaded engagement of groove guide 436 with the inner housing 108 (see FIG. 4). As in the previous embodiment a code digit of "1" denotes that a contact engages a conductive segment 302 whereas a code digit of "0" denotes that a contact engages a non-conductive segment 304. FIG. 16 depicts a numerical representation of track-A from which the unique eight bit binary codes associated with the various rotational positions of the encoded member 406 during dose dialling can be determined.

Figures 17, 18:
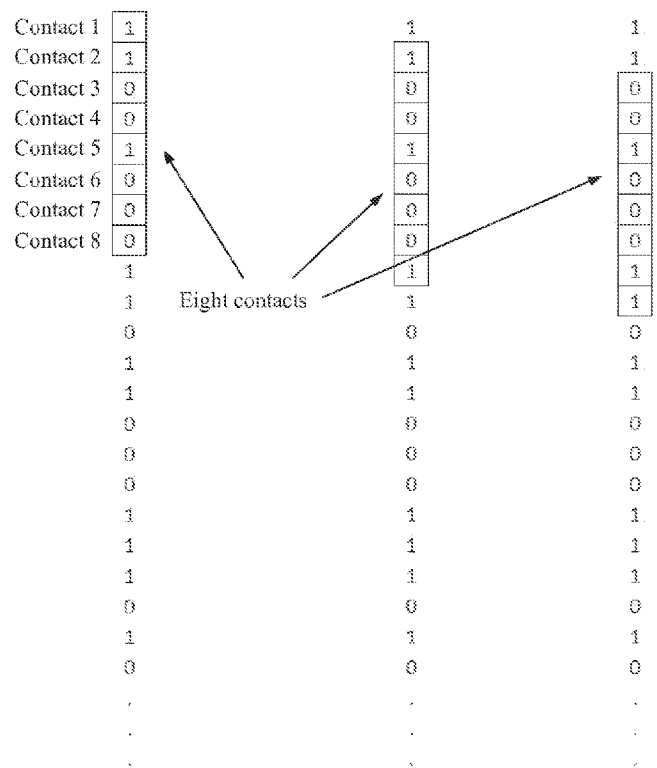
FIG. 17 shows a graphical representation of eight position-determining contacts 212a-212h (depicted as contacts 1 to 8) as they move over track-B in FIG. 13.
FIG. 18 shows a numerical representation of track-B in FIG. 14.

FIG. 17 illustrates how the eight position-determining contacts 212a-212h of the present embodiment (depicted as contacts 1-8) move into and out of engagement with conductive and non-conductive segments 302, 304 of track-B when the encoded member 406 is moved rotationally relative to the housing 102 in dispensing mode. Note that such rotational movement also causes the encoded member 406 to move axially due to the threaded engagement of groove guide 436 with the inner housing 108 (see FIG. 4). FIG. 18 depicts a numerical representation of track-B from which the unique eight bit binary codes associated with the various rotational positions of the encoded member 406 during dose dispensing can be determined.

How the processor 202 utilises the position-determining contacts 212a-212h to determine the absolute rotational position of the encoded member 406 is largely similar to the manner described in the foregoing embodiment except that since there are eight position-determining contacts, each rotational position of the encoded member 406 is instead associated with an eight bit binary code. In particular, the algorithm of applying voltages to respective position determining contacts one-by-one until at least one other such contact is detected as being energised is used but now with eight position-determining contacts 212a-212h.

When a voltage is applied to one of the position-determining contacts 212a-212h, if any other such contact is energised (as a result of being electrically coupled via the helical track 300) then the processor 202 can determine the eight bit binary code associated with the absolute rotational position of the encoded member 406. Once the unique eight bit binary code has been determined a look up table is consulted in the manner heretofore described to determine the amount of dose dialled or dispensed and whether the drug delivery device 100 is in dialling or dispensing mode.

Such a lookup table provides a conversion from the eight bit binary code result to a dose unit dialled or dispensed. More specifically the lookup table associates amounts of dose dialled (0, 1, 2 . . . 80 International Units) with respective eight bit binary code combinations provided by track-A. Furthermore the lookup table associates amounts of dose dispensed (0, 1, 2 . . . 80 International Units) with respective eight bit binary code combinations provided by track-B. Thus by reading an eight bit binary code from the encoded member at a particular point in time, the processor 202 can determine an amount of dose dialled or dispensed and whether the device 100 is in dialling mode or dispensing mode.

The processor 202 may determine the drug dose which has been dispensed (or is yet to be dispensed, if any) by subtracting a remaining drug dose from an initially dialled drug dose. The display 210 may be used to show the dose amount yet to be dispensed if a user does not dispense the full amount of a dialled dose.

Having determined the drug dose which has been dispensed, the processor 202 may store the result in the flash memory 205. As mentioned above the display 210 may be controlled to display the result of the dispensed dose determination. The display 210 may show the result of the dispensed dose determination for a predetermined time, for example 60 seconds. Alternatively or in addition, the dispensed dose history may be retrieved electronically from the flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Further envisaged arrangements of the second embodiment described herein will now be briefly outlined.

The processor 202 may implement the process of checking the contacts 212a-212h while the encoded member 406 is actually rotating, i.e. while the device 100 is actually being dialled or is being used to dispense a substance. Alternatively the checking process may only be performed when the processor 202 detects that the encoded member 406 has been in a certain position for a predetermined amount of time (for example 100 milliseconds), thereby indicating that the device 100 has been dialled or dispensed an intended amount by a user.

Also, the device 100 may be configured so that i) track-B is analysed by the position-determining contacts 212a-212h in dialling mode and ii) track-A is analysed by the position-determining contacts 212a-212h in dispensing mode.

Third Embodiment

It will be appreciated that in the foregoing embodiments the encoding system defined by i) the helical track 300 and ii) the position-determining contacts, is what enables the absolute rotational position of an encoded member 406 to be determined (which thereby enables the dialled/dispensed dose amount to be determined). However the encoding system need not necessarily be limited exclusively to electrically conductive members only.

For example, in an optical version of the second embodiment previously described in connection with FIG. 13, the encoding system could alternatively comprise i) a series of markings on the outer surface 440 of the encoded member 406 for defining the axially offset codes and ii) eight optical sensors. In particular, the optically readable codes may be located on an encoded member 406 such that the markings are located in similar positions to the conductive segments 302 in FIG. 13. Different markings may be of different colours and/or shapes.

In such an arrangement, which will be referred to hereafter as the third drug delivery device embodiment, the eight optical sensors may be positioned relative to the encoded member 406 in similar positions to the position-determining contacts 212a-212h. For instance the optical sensors may be configured to analyse corresponding parts of the encoded member's outer surface 440 which the position-determining contacts 212a-212h otherwise engage in the second embodiment. Due to axial float of the optical codes relative to the optical sensors, such sensors are arranged to analyse one of the two optical codes depending on the mode of operation of the device.

The optical sensors may take any suitable form. The optical sensors are configured to provide an output signal that is different when a marking is present in the area of the optically readable code to an output signal that is provided when a marking is not present in the area of the optically readable code. In this way, the sensor output indicates whether or not a marker is present at the relevant location on the optically readable code. The optical sensors may be active (for instance including an illuminating light source) or they may be passive (relying on ambient light to detect the code).

The processor 202 may be configured to continually observe outputs of the optical sensors when determining the absolute rotational position of the encoded member 406 and thus the dose dialled or dispensed. For instance by continually observing outputs of the optical sensors the processor 202 can determine the absolute rotational position of the encoded member 406 by directly analysing which optical sensors are directed towards a marking on the encoded member's outer surface 440. Such markings correspond with the conductive segments 302 previously described.

When a user of a drug delivery device 100 according to the third embodiment twists the rotatable dial 108 to set or dial in a drug dose, the processor 202 may be activated and may be controlled by software stored in the ROM 204 to apply a voltage to the optical sensors. The processor 202 may also be controlled by the software to execute a check on the optical sensors to determine which of them are directed towards a code marking on the encoded member 406. This enables the eight bit binary code associated with the absolute rotational position of the encoded member 406 to be directly determined by the processor 202. In particular, those sensors detected as being directed towards a code marking are associated with a code value of "1". The other sensors are associated with a code value of "0". Comparing this binary code with a lookup table in the manner heretofore described enables an amount of dose dialled to be determined. Similarly an amount of dose that has been dispensed (or is yet to be dispensed, if any) may be determined in a corresponding manner. Since the two optical codes define different eight bit binary code combinations, comparing a determined binary code with the lookup table enables the processor 202 to determine whether the drug delivery device 100 is in dialling or dispensing mode like in the second embodiment.

Having determined the drug dose which has been dispensed, the processor 202 may store the result in the flash memory 205. As mentioned above the display 210 may be controlled to display the result of the dispensed dose determination. The display 210 may show the result of the dispensed dose determination for a predetermined time, for example 60 seconds. Alternatively or in addition, the dispensed dose history may be retrieved electronically from the flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Figure 19:
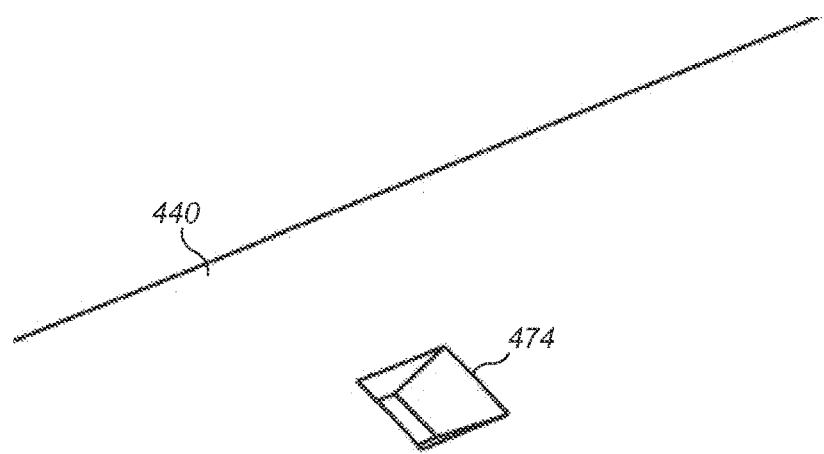
FIG. 19 shows an encoded member's outer surface 440 having a recess 474.

A drug delivery device 100, according to the third embodiment, may additionally be provided with a switch for switching the optical sensors off when the device is in a zero dose dialled position (i.e. when zero International Units of dose have been dialled and the dose delivery button 416 is not pressed). With reference to FIG. 19 such a switch may comprise i) a recess 474 in the encoded member's outer surface 440 and ii) an actuator (not shown). The actuator may be arranged to extend into the recess 474 when the encoded member 406 is in the aforementioned zero dose dialled position.

Figure 20:
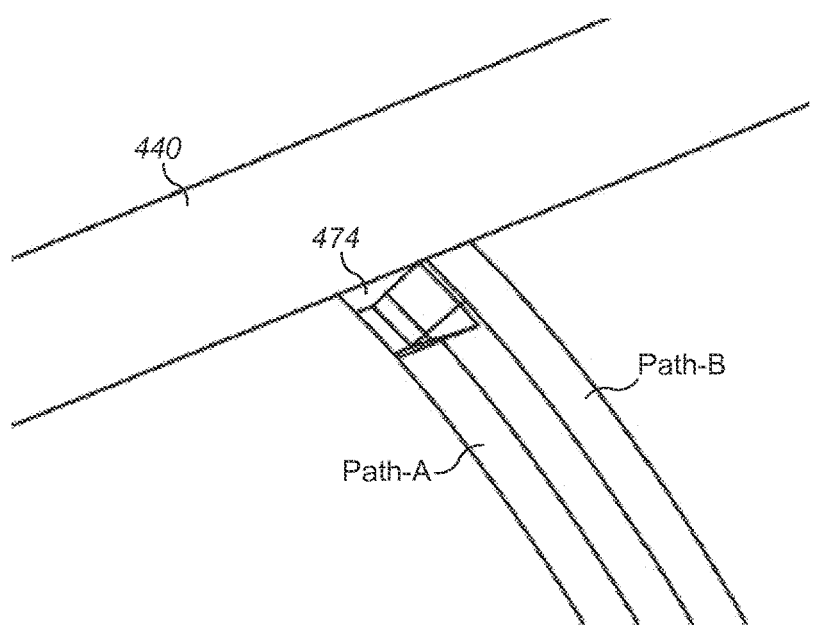
FIG. 20 depicts paths which an actuator may follow across the encoded member's outer surface 440 in FIG. 19.

Upon dialling a dose by twisting dial 108, thereby causing the encoded member 406 to rotate relative to the actuator (not shown), the actuator is caused to move (for example by sliding) upwards out of the recess and to follow helical path-A (see FIG. 20) as the encoded member's outer surface 440 brushes across it. Upon dispensing a dose, after the encoded member shifts axially (without rotating) in the before described manner, when the encoded member 406 rotates the actuator is caused to follow helical path-B (see FIG. 20) as the encoded member's outer surface 440 brushes across it. It will be appreciated that returning the drug delivery device 100 to the zero dose dialled configuration, and thus the encoded member 406 back to the zero dose dialled position, causes the actuator (not shown) to slide back into the recess 474.

The processor 202 is configured to detect whether or not the actuator (not shown) is located in the recess 474. When the actuator is detected as being located in the recess 474 the drug delivery device 100 is determined not to be in use and power is not supplied to the optical sensors. When the actuator is detected as being located outside of the recess 474 the drug delivery device 100 is determined to be in use and power is supplied to the optical sensors such that an amount of dose dialled or dispensed is able to be determined.

Further envisaged arrangements of the third embodiment described herein will now be briefly outlined. The processor 202 may implement the process of checking the optical sensors while the encoded member 406 is actually rotating, i.e. while the device 100 is actually being dialled or is being used to dispense a substance. Alternatively the checking process may only be performed when the processor 202 detects that the encoded member 406 has been in a certain position for a predetermined amount of time (for example 100 milliseconds), thereby indicating that the device 100 has been dialled or dispensed an intended amount by a user. Furthermore, markings of the optically readable codes may be arranged to define two axially offset Gray codes.

It will be appreciated that each of the foregoing drug delivery device embodiments have at least the following features a housing (such as housing 102, see FIG. 1); a plurality of sensors (for example electrical contacts such as those illustrated FIG. 9 or a plurality of optical sensors); and a cylindrical member (such as encoded member 406) supported within the housing, the outer surface of said cylindrical member being provided with a helical track (such as the track in FIG. 8, the track 300 in FIG. 13 or an optically readable track).

The helical track comprises track segments of a first type (for example electrically conductive segments 302) and track segments of a second type (for example electrically insulating segments 304, the part labelled D in FIGS. 10 and 11 comprising such an insulating segment 304).

The first and second types of track segment are respectively capable of inducing first and second responses in the sensors (in the case of a track which is analysed by optical sensors the first and second types of track segments may be different colours and/or different shapes).

The helical track has a width dimension (for example, see the length labelled W in FIGS. 10 and 14). The helical track includes across its width at least one track segment of the first type and at least one track segment of the second type at plural positions along the length of the helical track (at plural positions along the lengths of the helical tracks depicted in FIGS. 11 and 14 the tracks include across their respective widths different combinations of first and second types of track segments, see the parts labelled Y and Z for example).

The device is configured such that during a first phase of a drug delivery operation the helical track is moved axially, without rotation, relative to the plurality of sensors between a first position and a second position, and during a second phase of the drug delivery operation the track is moved helically relative to the plurality of sensors from the second position (for example in the case of FIG. 10 such axial movement causes electrical contacts to shift between helical paths which encompass areas A and B and helical paths which encompass areas C and D).

Also, responses induced in the plurality of sensors by the track segments of the helical track are different in the first position compared to responses induced in the plurality of sensors by the helical track in the second position (the sensors may have responses induced in them by different pluralities of sensors depending on whether the cylindrical member is in the first or second position relative to the sensors).

Finally, it will be appreciated that the above described embodiments are purely illustrative and are not limiting on the scope of the invention. Other variations and modifications will be apparent to persons skilled in the art upon reading the present application. For instance the code defined by the helical track in each of the foregoing embodiments may define a different combination of "0"s and "1"s to the tracks depicted in the drawings. Also, the actuator and recess arrangement discussed in connection with FIGS. 19 and 20 may be used in conjunction with any of the other device embodiments. In particular the actuator and recess arrangement may be used to control when a voltage sensor or any other device capable of detecting electrical signals should be turned on and/or off, or when the processor should and/or should not check an electrical contact to determine whether or not the contact has been energised.

In embodiments that use conductive track, sensing of the presence or absence of track is performed using a contact and the processor. At a general level, this may involve hardware that compares a voltage signal provided by the contact with a threshold and indicting the presence or absence of track through an output that indicates whether the voltage exceeded or did not exceed respectively the threshold. In a processor implementation, it may involve buffering the signal provided by the contact, for instance using an inverter gate or other buffer, sampling the buffered signal and comparing the sampled signal to a reference. Other ways of sensing the presence or absence of track will be apparent to the skilled person.

Figure 21:
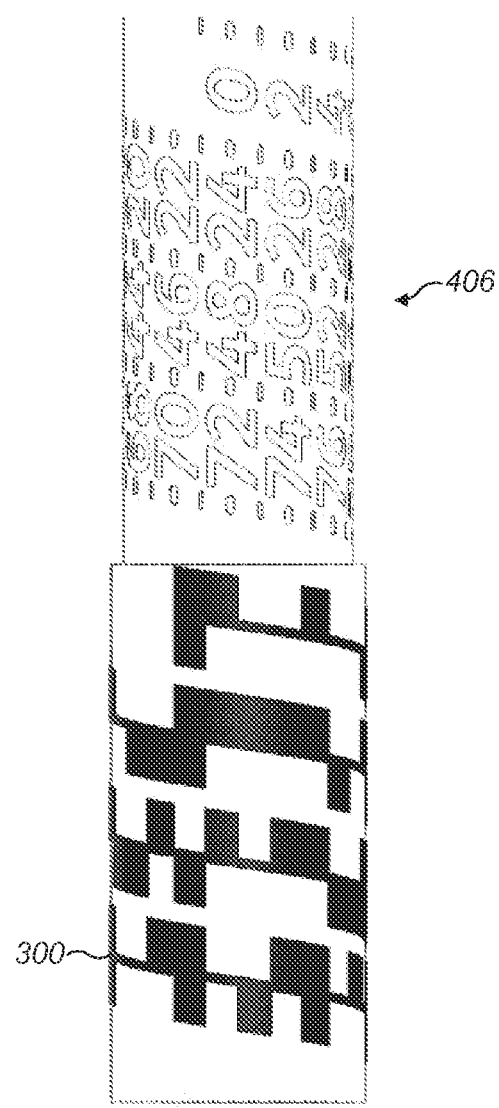
FIG. 21 depicts an external view of an alternative encoded member embodiment.

Each of the foregoing embodiments may be configured such that the track (whether it is electrically conductive or optically readable) is not exposed when a dose is dialled. In particular, when a dose is dialled the encoded member 406 is caused to rotate thereby causing it to move in a direction away from housing 102 (see FIG. 1). However the track may be provided on the encoded member 406 such that it does not leave the volume encompassed by the housing 102 upon rotation of the encoded member 406. In such an arrangement, illustrated in FIG. 21, one or more numbers for indicating a dose dialled may be caused to be exposed instead, with the helical track remaining hidden within the injection device even when the maximum dose is dialled in. It should be noted that the helical track 300 need not necessarily be of the configuration depicted in FIG. 21 and may instead have a configuration according to the first embodiment (in FIG. 8) for example.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A drug delivery device comprising:
a housing;
a plurality of sensors; and
a cylindrical member supported within the housing, an outer surface of the cylindrical member being provided with a helical track, the helical track comprising track segments of a first type and track segments of a second type, the first and second types of track segments being respectively capable of inducing first and second responses in the sensors;
wherein:
the helical track has a width;
the helical track includes across the width of the helical track at least one track segment of the first type and at least one track segment of the second type at plural positions along a length of the helical track;
the device is configured such that during a first phase of a drug delivery operation the helical track is moved axially, without rotation, relative to the plurality of sensors between a first position in which the plurality of sensors engage the at least one track segment of the first type and a second position in which the plurality of sensors engage the at least one track segment of the second type, and during a second phase of the drug delivery operation the track is moved helically relative to the plurality of sensors from the second position; and
responses induced in the plurality of sensors by the track segments of the helical track are different in the first position compared to responses induced in the plurality of sensors by the helical track in the second position,
wherein the drug delivery device further comprises a processor configured to:
receive and interpret electrical signals from each of the plurality of sensors to determine a position of the cylindrical member relative to the housing; and
determine a selected drug dose by searching a lookup table which provides a conversion between a rotational position of the cylindrical member relative to the housing and the selected drug dose.

2. The device of claim 1, wherein the plurality of sensors are arranged to have a response induced in them by first and second pluralities of the track segments when the helical track is in the first and second positions relative to the sensors respectively.

3. The device of claim 2, wherein at least one track segment in the first plurality of track segments is of a different type compared to the track segments in the second plurality of track segments.

4. The device of claim 1, wherein the device is configured such that the helical track may be moved relative to the sensors along first and second helical paths that are axially offset relative to one another.

5. The device of claim 4, the device being configured such that in use responses induced in the plurality of sensors by the track segments as the helical track moves along the first helical path are different to those induced in the plurality of sensors by the track segments as the helical track moves along the second helical path.

6. The device of claim 4, wherein the device is configured such that during the first phase of the drug delivery operation the helical track is moved axially, without rotation, relative to the plurality of sensors between a first position located on the first helical path and a second position located on the second helical path, and during the second phase of the drug delivery operation the helical track is moved along the second helical path.

7. The device of claim 1, wherein the plurality of sensors comprises eight sensors.

8. The device of claim 1, wherein the helical track comprises a first track segment of the first type at a first location on the width of the helical track for the whole of the length of the helical track, and a second track segment of the second type at a second location on the width of the helical track for the whole of the length of the helical track.

9. The device of claim 8, wherein the first track segment is able to induce a first response in a sensor of the plurality of sensors when the helical track is in the first position relative to the sensors, and the second track segment is able to induce a second response in the sensor when the helical track is in the second position relative to the sensors.

10. The device of claim 1, further comprising a detector for detecting when a dose is being dialed and when the dialed dose has been fully dispensed, the detector being able to cause power to be supplied to the sensors when the dose is being dialed and to cause power not to be supplied to the sensors when the dialed dose has been fully dispensed.

11. The device of claim 10, wherein the detector comprises first and second parts of a two-part mechanism, wherein the first part is located on the cylindrical member, the detector being configured such that the first and second parts thereof only engage one another when the dose has not been dialed or the dialed dose has been fully dispensed.

12. The device of claim 1, wherein the processor is configured to determine an operational mode of the drug delivery device by searching a lookup table which provides a conversion between the position of the cylindrical member relative to the housing and the operational mode of the drug delivery device.

* * * * *